United States Patent
Chiu et al.

(10) Patent No.: US 12,319,909 B2
(45) Date of Patent: *Jun. 3, 2025

(54) COMPOSITIONS AND METHODS FOR RIBONUCLEIC ACID EXTRACTION

(71) Applicant: Phase Scientific International, Ltd., Hong Kong (CN)

(72) Inventors: Yin To Chiu, Hong Kong (CN); Harsha Madan Kittur, Hong Kong (CN); Cheuk Yiu Tenny Chung, Hong Kong (CN); Garrett Lee Mosley, Hong Kong (CN)

(73) Assignee: Phase Scientific International, Ltd., Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/249,936

(22) Filed: Mar. 19, 2021

(65) Prior Publication Data

US 2021/0292743 A1    Sep. 23, 2021

Related U.S. Application Data

(60) Provisional application No. 62/992,222, filed on Mar. 20, 2020.

(51) Int. Cl.
*C12N 15/10* (2006.01)

(52) U.S. Cl.
CPC .................. *C12N 15/1003* (2013.01)

(58) Field of Classification Search
CPC ....... C12N 15/1003; C12Q 1/68; G01N 33/48
USPC ........................................ 536/25.4
See application file for complete search history.

(56) References Cited

U.S. PATENT DOCUMENTS

| | | | |
|---|---|---|---|
| 3,728,285 A * | 4/1973 | Brindell et al. | C08G 65/12 528/402 |
| 6,132,763 A | 10/2000 | Fisher | |
| 6,399,385 B1 | 6/2002 | Croyle et al. | |
| 7,626,017 B2 | 12/2009 | Laugharn, Jr. et al. | |
| 7,666,583 B2 | 2/2010 | Mor et al. | |
| 7,803,405 B2 | 9/2010 | Keating et al. | |
| 9,823,247 B2 | 11/2017 | Kamei et al. | |
| 10,006,911 B2 | 6/2018 | Kamei et al. | |
| 10,359,423 B2 | 7/2019 | Kamei et al. | |
| 10,578,616 B2 | 3/2020 | Kamei et al. | |
| 11,287,426 B2 | 3/2022 | Kamei et al. | |
| 11,327,075 B2 | 5/2022 | Kamei et al. | |
| 11,332,796 B2 * | 5/2022 | Chiu | C12Q 1/6886 |
| 2002/0042506 A1 | 4/2002 | Kristyanne et al. | |
| 2005/0077497 A1 | 4/2005 | Anderson | |
| 2006/0025579 A1 | 2/2006 | Riedl et al. | |
| 2006/0166349 A1 | 7/2006 | Kepka et al. | |
| 2007/0161000 A1 | 7/2007 | Van Alstine et al. | |
| 2008/0242825 A1 | 10/2008 | Devi et al. | |
| 2009/0192111 A1 | 7/2009 | Bader et al. | |
| 2009/0286966 A1 | 11/2009 | Christensen et al. | |
| 2010/0174052 A1 | 7/2010 | Hjorth et al. | |
| 2010/0179252 A1 | 7/2010 | Johansson et al. | |
| 2011/0257378 A1 | 10/2011 | Tran et al. | |
| 2011/0263040 A1 | 10/2011 | Jones | |
| 2013/0164825 A1 | 6/2013 | Christoffel et al. | |
| 2014/0121357 A1 | 5/2014 | Segura Ruiz et al. | |
| 2014/0221549 A1 | 8/2014 | Bodkhe et al. | |
| 2014/0227712 A1 | 8/2014 | Horlitz et al. | |
| 2014/0228549 A1 | 8/2014 | Burghoff et al. | |
| 2015/0166592 A1 | 6/2015 | Guo | |
| 2015/0253320 A1 | 9/2015 | Kamei et al. | |
| 2018/0100854 A1 | 4/2018 | Kamei et al. | |
| 2018/0258419 A1 | 9/2018 | Fischer et al. | |
| 2018/0259521 A1 | 9/2018 | Kamei et al. | |
| 2019/0033308 A1 | 1/2019 | Kamei et al. | |
| 2019/0187140 A1 | 6/2019 | Kamei et al. | |
| 2019/0250156 A1 | 8/2019 | Kamei et al. | |
| 2019/0391143 A1 | 12/2019 | Kamei et al. | |
| 2020/0150116 A1 | 5/2020 | Kamei et al. | |
| 2020/0284791 A1 | 9/2020 | Kamei et al. | |
| 2022/0252598 A1 | 8/2022 | Kamei et al. | |

FOREIGN PATENT DOCUMENTS

| | | |
|---|---|---|
| CN | 101679481 A | 3/2010 |
| CN | 101835790 A | 9/2010 |
| CN | 102264901 A | 11/2011 |
| CN | 102272144 A | 12/2011 |
| CN | 102421898 A | 4/2012 |
| CN | 103476786 A | 12/2013 |
| CN | 103797023 A | 5/2014 |
| CN | 104707358 A | 6/2015 |
| CN | 106662582 A | 5/2017 |
| CN | 110003323 A | 7/2019 |
| CN | 111304291 A | 6/2020 |

(Continued)

OTHER PUBLICATIONS

Rio et al, Cold Spring Harb Protoc, 2010, 6, pp. 1-4.*
Czimmerer et al, PLoS One, 2013, 8(1), 1-10.*
Luechau et al, Separation and Purification Technology, 2009, 66, 397-404.*
Tang et al, CN 108342383A, Machine English Translation, pp. 1-8.*
Frerix et al, Biotechnol. Appl. Biochem. 2005, 42, 57-66.*
Chomczynski et al, Nature Protocols, 2006, 1(2), 581-585.*
Ziegler YS, et al. (2014) Plasma membrane proteomics of human breast cancer cell lines identifies potential targets for breast cancer diagnosis and treatment. PLoS One. 9(7):e102341.
Schindler J, et al. (2008) Aqueous polymer two-phase systems for the proteomic analysis of plasma membranes from minute brain samples. J Proteome Res 7(1):432-442.

(Continued)

*Primary Examiner* — Ganapathy Krishnan
(74) *Attorney, Agent, or Firm* — EAGLE IP LIMITED (57) ABSTRACT

This invention relates to the isolation, concentration and/or purification of ribonucleic acid (RNA) in aqueous two-phase phase systems. In some embodiments, the present invention provides sample preparation methods, compositions and kit components for the isolation, concentration and/or purification of RNA from fluid mixtures comprising biological materials.

24 Claims, 2 Drawing Sheets

(56) References Cited

FOREIGN PATENT DOCUMENTS

| | | | |
|---|---|---|---|
| EP | 0268946 A2 | 6/1988 | |
| JP | 2000245460 A | 9/2000 | |
| JP | 2002537106 A | 11/2002 | |
| JP | 2007525222 A | 9/2007 | |
| JP | 2017513015 A | 5/2017 | |
| NO | 2011169537 A2 | 12/2011 | |
| WO | 0050161 A1 | 8/2000 | |
| WO | 2002057289 A1 | 7/2002 | |
| WO | WO 02/057289 A1 * | 7/2002 | ............... C12Q 1/68 |
| WO | 2007140417 A2 | 12/2007 | |
| WO | 2014128129 A1 | 8/2014 | |
| WO | 2015134938 A1 | 9/2015 | |
| WO | 2016155888 A1 | 10/2016 | |
| WO | 2017041030 A1 | 3/2017 | |
| WO | 2017214315 A1 | 12/2017 | |
| WO | 2018039139 A1 | 3/2018 | |
| WO | 2018183454 A1 | 10/2018 | |
| WO | 2018183465 A1 | 10/2018 | |
| WO | 2018222972 A1 | 12/2018 | |
| WO | 2019046553 A1 | 3/2019 | |
| WO | 2019046563 A1 | 3/2019 | |
| WO | WO 2019/055926 A2 * | 3/2019 | ............... C12Q 1/68 |
| WO | 2019118705 A1 | 6/2019 | |
| WO | 2019118712 A1 | 6/2019 | |
| WO | 2019143895 A1 | 7/2019 | |
| WO | 2019143943 A2 | 7/2019 | |
| WO | 2019144016 A1 | 7/2019 | |
| WO | WO 2019/144030 A1 * | 7/2019 | ............... C12Q 1/68 |
| WO | 2021037075 A1 | 3/2021 | |
| WO | 2021148393 A1 | 7/2021 | |
| WO | 2021185336 A1 | 9/2021 | |
| WO | 2022008591 A1 | 1/2022 | |

OTHER PUBLICATIONS

Spindler KL, et al. (2015) Circulating free DNA as biomarker and source for mutation detection in metastatic colorectal cancer. PLoS One. 10(4):e0108247.

Riedl W, et al. (2008) Membrane-supported extraction of biomolecules with aqueous two-phase systems[J]. Desalination, 224(1-3): 160-167.

Frerix A, et al. (2005) Scalable recovery of plasmid DNA based on aqueous two-phase separation. Biotechnol Appl Biochem. 42(Pt 1):57-66.

Crucho Cic, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal microcapsules for the management of lepidopteran pests of Brassica crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

Luechau, Frank; et al. (2009) Primary capture of high molecular weight nucleic acids using aqueous two-phase systems. Separation and purification technology, 66.1: 202-207.

Nazer, Behzad; et al. (2017) Plasmid DNA affinity partitioning using polyethylene glycol-sodium sulfate aqueous two-phase systems. Journal of Chromatography B, 1044: 112-119.

Sorber L, et al. (2017) A Comparison of Cell-Free DNA Isolation Kits: Isolation and Quantification of Cell-Free DNA in Plasma. J Mol Diagn. Jan. 19(1):162-168.

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, Plos One, Dec. 18, 2020, p. e0244271, vol. 15, No. 12.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Ricky Y. T. Chiu, et al., An Aqueous Two-Phase System for the Concentration and Extraction of Proteins from the Interface for Detection Using the Lateral-Flow Immunoassay, Plos One, Nov. 10, 2015, 1-14, Plos, California, US.

K. Jessie, et al., Protein Precipitation Method for Salivary Proteins and Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 No. 6, IRL Press Limited, Oxford, England.

Wu et al., "Factors Affecting Aqueous Two-Phase Extraction", Biopharmaceutical Technology (Fourth Edition), Aug. 2015, p. 122-126, China medicine science and technology press.

Filip Janku; et al., "A novel method for liquid-phase extraction of cell-free DNA for detection of circulating tumor DNA", Scientific reports, 2021, 11(1): 19653.

Ivanenko et al., "Synthesis of pharmacologically active hydrogels based on combined silicon and titanium polyolates", Russian Chemical Bulletin, International Edition, 2012, 61(11), pp. 2163-2171.

Gu et al., "Effect of particle size in a colloidal hydrogel scaffold for 3D cell culture", Colloids and Surfaces B: Biointerfaces, 2015, 136, p. 1139-1147.

Radi, B., "Reinforced hydrogels for silicone copolymer delivery for scar remediation", 2010, PhD thesis, Queensland University of Technology, 255 pages.

Khonani et al., "Synthesis of hydrogels based on silicon polyolates", Russian Chemical Bulletin, International Edition, 2010, 59(1), pp. 75-80.

Shin Hyunwoo et al., "Aqueous two-phase system to isolate extracellular vesicles from urine for prostate cancer diagnosis", Plos One, vol. 13, No. 3, Mar. 27, 2018 (Mar. 27, 2018), p. 0194818.

Pereira Matheus M. et al., "Pre-treatment strategies based on aqueous two-phase systems comprising ionic liquids to improve the

(56) References Cited

OTHER PUBLICATIONS adrenal cancer diagnosis", Journal of Molecular Liquids, vol. 367, Sep. 22, 2022, p. 120409, XP093103949.

Mendes Maria S. M. et al., "Aqueous two-phase systems as multipurpose tools to improve biomarker analysis", Separation and Purification Technology, vol. 317, Apr. 17, 2023 (Apr. 17, 2023), p. 123875, XP093103947.

Lee, Hoyoon, et al., "Precision cell-free DNA extraction for liquid biopsy by integrated microfluidics." NPJ precision oncology 4.1 (2020): 3.

Ahmed et al., "Aqueous Two-Phase Systems and Microfluidics for Microscale Assays and Analytical Measurements", Annual Review of Analytical Chemistry, 2021 14:1, 231-255.

Fei Yu, et al., "Comparative Evaluation of Three Preprocessing Methods for Extraction and Detection of Influenza A Virus Nucleic Acids from Sputum", Front Med (Lausanne), 2018 year, vol. 5:56.

Ribeiro et al., "Isolation of Plasmid DNA from Cell Lysates by Aqueous Two-Phase Systems", Published Mar. 15, 2002, Biotechnology and Bioengineering, vol. 78, Issue 4, pp. 376-384 (Year: 2002).

Lis et al., "Size fractionation of double-stranded DNA by precipitation with polyethylene glycol", Published Mar. 1, 1975, Nucleic Acids Research, vol. 2, Issue 3, pp. 383-390 (Year: 1975).

\* cited by examiner

COMPOSITIONS AND METHODS FOR RIBONUCLEIC ACID EXTRACTION

CROSS-REFERENCE TO RELATED APPLICATION

This application claims priority to, and the benefit of, U.S. Provisional Application Ser. No. 62/992,222 filed Mar. 20, 2020, entitled "COMPOSITIONS AND METHODS FOR RIBONUCLEIC ACID EXTRACTION". The entire contents of the foregoing application are hereby incorporated by reference for all purposes.

FIELD OF THE INVENTION

This invention relates to the isolation, concentration and/or purification of ribonucleic acid (RNA) in aqueous two-phase phase systems. In some embodiments, the present invention provides sample preparation methods, compositions and kit components for the isolation, concentration and/or purification of viral RNA from fluid mixtures comprising biological materials.

BACKGROUND

The need to test the presence of a virus quickly is of utmost importance during a viral outbreak or pandemic. Current diagnostic tests for detecting RNA, such as viral RNA, require high quality samples with sufficiently concentrated amounts of RNA in order to provide a good signal-to-noise ratio for downstream applications, such as testing for the presence of a viral disease in a patient. Current methods can only handle small amounts of biological sample (resulting in testing samples having very little viral RNA present) or require the use of multiple purification steps (e.g., column-based extraction), in order to isolate sufficient RNA for testing. Additionally, these methods are expensive, have slower turnaround times, and are not easily available.

Accordingly, there is a need for new technologies that are simpler, less expensive, and can quickly and accurately provide high quality RNA samples, such as for viral RNA diagnostic tests.

SUMMARY OF THE INVENTION

Disclosed herein are novel methods, compositions and kits for isolation, concentration and/or purification of RNA, such as viral RNA, employing aqueous two-phase systems (ATPS) without the need of complex equipment. The methods and compositions can achieve the following multiple tasks, including lysis, removing contaminants, and/or concentrating targeted analytes, such as viral RNA.

Some embodiments provide a method for isolating and concentrating viral ribonucleic acids from a fluid biological mixture including viral ribonucleic acids and contaminants. Examples of contaminants include, but are not limited to, ribonucleases, deoxyribonucleases, proteases, and albumin. In certain embodiments, contaminants include, but are not limited to, proteins, ribonucleases, deoxyribonucleases, proteases, albumin, lysing reagents, lysing salts, NaCl, KCl, $(NH_4)_2SO_4$, ammonium chloride, detergents, amphipathic molecules, non-ionic detergents, anionic detergents, cationic detergents, zwitterionic detergents, Triton X-100, Nonidet P-40, sodium deoxycholate, CHAPS, SDS, ethyl trimethyl ammonium bromide, metal ions, carbohydrates, glycerol, metal chelators, EDTA, reducing agents, Tris-2-carboxyethylphosphine hydrochloride (TCEP), carbon, cyanides, carbon monoxide, dithiothreitol (DTT), phosphites, hypophosphites, phosphorous acid, reducing sugars, ascorbic acid, formic acid, oxalic acid, diisobutylaluminum hydride, hydrazine, hydrogen peroxide, iodides, thiosulfates, dithionates, sulfur dioxide, sulfite compounds, compounds containing the Sn2+ ion, compounds containing the Fe2+ ion, sodium borohydride, diborane, zinc amalgam, sodium-lead alloy, sodium amalgam, nascent (atomic) hydrogen, lithium aluminum hydride, mercaptoethanol, ionic salts, non-ionic salts, or any combination thereof.

Possible polymers that may be employed include, but are not limited to, polyethylene glycols (PEGs), hydrophobically modified polyethylene glycols, poly(oxyalkylene)polymers, poly(oxyalkylene)copolymers, hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide or any combination thereof. Possible surfactants that may be employed include but are not limited to Triton-X, Triton-114, Igepal CA-630 and Nonidet P-40, anionic surfactants, such as carboxylates, sulphonates, petroleum sulphonates, alkylbenzenesulphonates, naphthalenesulphonates, olefin sulphonates, alkyl sulphates, sulphates, sulphated natural oils & fats, sulphated esters, sulphated alkanolamides, alkylphenols, ethoxylated and sulphated, non-ionic surfactants, such as ethoxylated aliphatic alcohol, polyoxyethylene surfactants, carboxylic esters, polyethylene glycol esters, anhydrosorbitol ester, glycol esters of fatty acids, carboxylic amides, monoalkanolamine condensates, polyoxyethylene fatty acid amides, cationic surfactants, such as quaternary ammonium salts, amines with amide linkages, polyoxyethylene alkyl & alicyclic amines, n,n,n',n' tetrakis substituted ethylenediamines, 2-alkyl 1-hydroxyethyl 2-imidazolines, and amphoteric surfactants, such as n-coco 3-aminopropionic acid/sodium salt, n-tallow 3-iminodipropionate, disodium salt, n-carboxymethyl n dimethyl n-9 octadecenyl ammonium hydroxide, n-cocoamidethyl n hydroxyethylglycine, and sodium salt.

Suitable salt component includes inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium; inorganic salts containing anions such as phosphate, sulphate, nitrate, chloride and hydrogen carbonate; a kosmotropic salt, a chaotropic salt, a magnesium salt, a lithium salt, a sodium salt, a potassium salt, a cesium salt, a zinc salt, an aluminum salt, a bromide salt, an iodide salt, a fluoride salt, a carbonate salt, a sulfate salt, a citrate salt, a carboxylate salt, a borate salt, a phosphate salt, NaCl, $Na_2SO_4$, potassium citrate, sodium citrate, sodium acetate, sodium phosphate, potassium phosphate, ammonium sulfate, and ammonium acetate.

In yet another embodiment, a kit is disclosed for isolating and concentrating viral ribonucleic acids from a fluid mixture including viral ribonucleic acids and contaminants. The kit may include the composition components described in the composition embodiment, but additionally syringe or pipette accessible containers for storage, packing, and/or reactions and optionally equipment for manipulating the aqueous solutions. Such containers and equipment may include columns, test tubes capillary tubes, plastic test tubes, falcon tubes, culture tubes, well plates, pipettes and/or cuvettes.

Advantages of the Current Invention

In certain embodiments, the disclosed compositions and methods have several advantages over the current solutions. For example, current RNA purification methods require multiple steps and rely on solid-liquid phase based interactions, such as column-based or bead-based extraction methods. These techniques require large amounts of sample in order to obtain enough RNA to generate an accurate result on a molecular assay. The current method does not require a column or beads.

Additionally, in certain embodiments, the disclosed compositions and methods are able to process and extract a wide range of fluid mixture volumes. They can take a large variety of different types of viral transfer media (VTM). Furthermore, in certain embodiments, they can handle large volumes of VTM (e.g., up to several milliliters) and are able to process the entire volume efficiently, thus providing a larger amount of clean, purified RNA sample for testing.

Furthermore, in certain embodiments, the disclosed compositions and methods are able to resuspend the RNA in a variable amount of fluid and in a broad variety of solutions. The variable volume allows for a higher concentration of the target RNA which may improve downstream analysis. The flexibility of the choice of resuspension solution may also help with downstream analysis by enabling a compatible buffer to be chosen for the downstream analysis system. Current column and bead based systems do not benefit from this, as their elution buffers have inflexible composition requirements, and they have higher elution volume requirements.

Finally, in certain embodiments, the disclosed compositions and methods are surprisingly effective at extracting ribonucleic acid components from a fluid mixture full of contaminants. Surprisingly, they can successfully isolate the ribonucleic acid components without the use of separate reducing agents or carrier nucleic acids.

These and other features and characteristics, as well as the methods of operation and functions of the related components and economies of manufacture, will become more apparent upon consideration of the following detailed description and the appended claims with reference to the accompanying figures, all of which form a part of this specification, wherein like reference numerals designate corresponding parts in the various figures. It is to be expressly understood, however, that the drawings are for the purpose of illustration and description only and are not intended as a definition of the limits of the claims. As used in the specification and in the claims, the singular form of "a", "an", and "the" include plural referents unless the context clearly dictates otherwise

DETAILED DESCRIPTION

Unless indicated otherwise, the terms used herein, including technical and scientific terms, have the same meaning as usually understood by those skilled in the art to which the present invention pertains and detailed descriptions of well-known functions and constitutions that may obscure the gist of the present invention are omitted.

'Aqueous,' as used herein, refers to the characteristic properties of a solvent/solute system wherein the solvating substance has a predominantly hydrophilic character. Examples of aqueous solvent/solute systems include those where water, or compositions containing water, are the predominant solvent. The polymer and/or surfactant components whose use is described in the embodiments are "aqueous" in the sense that they form aqueous phases when combined with a solvent such as water. Further, as understood by the skilled person, in the present context the term liquid "mixture" refers merely to a combination of the herein-defined components.

As used herein, an aqueous two-phase system (ATPS) means a liquid-liquid separation system that can accomplish isolation or concentration of an analyte by partitioning, where two phases, sections, areas, components, or the like, interact differently with at least one analyte to which they are exposed and optionally dissolved. An ATPS is formed when two immiscible phase forming components, such as salt and polymer, or two incompatible polymers (e.g., PEG and dextran) with a certain concentration are mixed in an aqueous solution. ATPS methods are relatively inexpensive and scalable because they employ two-phase partitioning to separate analytes (e.g., nucleic acids) from contaminants.

The term 'isolated' as used herein refers to nucleic acid removed from its original environment and thus is altered from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components).

As used herein, 'concentrated' means that the mass ratio of analyte in question to the solution in which the analyte is suspended is higher than the mass ratio of said analyte in its pre-concentration solution. It can, for example, be slightly higher, or more preferably at least twice, ten times or one hundred times as high.

As used herein, 'polymer' includes, but is not limited to, homopolymer, copolymer, terpolymer, random copolymer, and block copolymer. Block copolymers include, but are not limited to, block, graft, dendrimer, and star polymers. As used herein, copolymer refers to a polymer derived from two monomeric species; similarly, a terpolymer refers to a polymer derived from three monomeric species. The polymer also includes various morphologies, including, but not limited to, linear polymer, branched polymer, random polymer, crosslinked polymer, and dendrimer systems. As an example, polyacrylamide polymer refers to any polymer including polyacrylamide, e.g., a homopolymer, copolymer, terpolymer, random copolymer, block copolymer or terpolymer of polyacrylamide. Polyacrylamide can be a linear polymer, branched polymer, random polymer, crosslinked polymer, or a dendrimer of polyacrylamide.

Embodiments of the Present Invention

One aspect provides a method for isolating ribonucleic acid components from a fluid mixture including ribonucleic acid components and contaminants, comprising:

a) adding said fluid mixture to an aqueous two-phase system (ATPS) comprising a first phase solution and a second phase solution, such that the ribonucleic acids partition to the first phase solution and said contaminants partition to the second phase solution; and b) isolating the ribonucleic acid components from the first phase solution.

In some embodiment, the ribonucleic acid components are ribonucleic acids or ribonucleic acid fragments. In some embodiments, the ribonucleic acid fragments are under 250 bp.

Some embodiments further comprise the step of a lysis process, wherein the lysis process comprises the following steps:

a) providing a biological sample;

b) mixing the biological sample with lysing reagents to form a sample mixture;

c) incubating the sample mixture to arrive at the fluid mixture including ribonucleic acid components and contaminants.

In some embodiments, the lysis step is done before the isolation step described above. In some embodiments, the biological sample is obtained from a subject, such as a patient, before the lysis step.

In some embodiments, the biological sample comprises biological material that releases ribonucleic acid components when subject to the lysis process described herein. In some embodiments, the biological material is selected from one or more of the following: viruses, eukaryotic cells, prokaryotic cells, protein coats, vesicles, RNA complexed with proteins, tertiary RNA structures, and un-complexed RNA. In some embodiments, the biological material is a virus. In other embodiments, the virus is an enveloped virus with a lipid bilayer. In yet other embodiments, the virus has a target RNA sequence that is greater than 25 kilobases. In some embodiments, the virus has a target viral RNA that is in complex in a nucleocapsid within the viral envelope of said virus.

In certain embodiments, the virus is selected from one or more of the following: Yueviridae, Xinmoviridae, Wupedeviridae, Virgaviridae, Tymoviridae, Turriviridae, Tristromaviridae, Totiviridae, Tospoviridae, Tombusviridae, Tolecusatellitidae, Togaviridae, Tobaniviridae, Tectiviridae, Sunviridae, Spiraviridae, Sphaerolipoviridae, Solinviviridae, Solemoviridae, Smacoviridae, Siphoviridae, Secoviridae, Sarthroviridae, Rudiviridae, Roniviridae, Rhabdoviridae, Retroviridae, Reoviridae, Quadriviridae, Qinviridae, Pseudoviridae, Poxviridae, Potyviridae, Pospiviroidae, Portogloboviridae, Polyomaviridae, Polydnaviridae, Polycipiviridae, Podoviridae, Pneumoviridae, Pleolipoviridae, Plasmaviridae, Picornaviridae, Picobirnaviridae, Phycodnaviridae, Phenuiviridae, Phasmaviridae, Permutotetraviridae, Peribunyaviridae, Parvoviridae, Partitiviridae, Paramyxoviridae, Papillomaviridae, Ovaliviridae, Orthomyxoviridae, Nyamiviridae, Nudiviridae, Nodaviridae, Nimaviridae, Narnaviridae, Nanoviridae, Nairoviridae, Mypoviridae, Myoviridae, Mymonaviridae, Mononiviridae, Mimiviridae, Microviridae, Metaviridae, Mesoniviridae, Megabirnaviridae, Medioniviridae, Matonaviridae, Marseilleviridae, Marnaviridae, Malacoherpesviridae, Luteoviridae, Lispiviridae, Lipothrixviridae, Leviviridae, Leishbuviridae, Lavidaviridae, Kitaviridae, Iridoviridae, Inoviridae, Iflaviridae, Hytrosaviridae, Hypoviridae, Herpesviridae, Herelleviridae, Hepeviridae, Hepadnaviridae, Hantaviridae, Guttaviridae, Globuloviridae, Genomoviridae, Geminiviridae, Gammaflexiviridae, Fuselloviridae, Flaviviridae, Fimoviridae, Filoviridae, Euroniviridae, Endornaviridae, Dicistroviridae, Deltaflexiviridae, Cystoviridae, Cruliviridae, Corticoviridae, Coronaviridae, Closteroviridae, Clavaviridae, Circoviridae, Chuviridae, Chrysoviridae, Caulimoviridae, Carmotetraviridae, Caliciviridae, Bromoviridae, Botourmiaviridae, Bornaviridae, Birnaviridae, Bidnaviridae, Bicaudaviridae, Betaflexiviridae, Benyviridae, Belpaoviridae, Barnaviridae, Baculoviridae, Bacilladnaviridae, Avsunviroidae, Astroviridae, Aspiviridae, Asfarviridae, Ascoviridae, Artoviridae, Arteriviridae, Arenaviridae, Anelloviridae, Ampullaviridae, Amnoonviridae, Amalgaviridae, Alvernaviridae, Alphatetraviridae, Alphasatellitidae, Alphaflexiviridae, Alloherpesviridae, Adenoviridae, Ackermannviridae, and Abyssoviridae.

In some embodiments, the Coronaviridae is SAR-CoV, SARS-CoV-2, or MERS-CoV.

In some embodiments, the SAR-CoV-2 comprises variants selected from one or more of the following: B.1.526, B.1.525, P.2, B.1.1.7, P.1, B.1.351, B.1.427, and B.1.429.

In some embodiments, the fluid mixture is 1 uL to 1000 uL. In some embodiments, the fluid mixture is 500 uL-1000 uL. In some embodiments, the fluid mixture is 150 uL-1000 uL. In some embodiments, the fluid mixture is 1000 uL.

Another embodiment further comprises the step of collecting the biological sample from a subject Biological samples can be obtained in a number of ways from subjects, such as patients.

In some embodiments, the biological sample is selected from one or more of the following: throat swab, nasal swab, saliva swab, saliva sample, stimulate saliva sample, expectorated sputum, bile sample, urine sample, vaginal swab, endocervical swab, urethral swab, semen sample, blood sample, plasma sample, serum sample, fecal sample, cerebral spinal fluid, lacrimal fluid sample, perspiration fluid sample, amniotic fluid sample, or tissue biopsy. In other embodiments, the biological sample is selected from saliva, expectorated sputum, urine, bile, vaginal fluid, endocervical fluid, urethral fluid, semen, blood, plasma, serum, feces, cerebral spinal fluid, lacrimal fluid, perspiration, amniotic fluid, or a tissue biopsy.

In yet another embodiment isolating the ribonucleic acid components from the first phase solution comprises the following steps:

a) mixing the first phase solution with RNA precipitation components to form a mixed solution;

b) centrifuging the mixed solution to form a pellet containing the ribonucleic acid; and c) re-suspending the pellet containing the ribonucleic acid in a resuspension fluid to form a re-suspended pellet.

In some embodiments, the first phase is first separated from the second phase solution before mixing with the RNA precipitation components.

In some embodiments, the volume of the resuspension fluid is 5 uL-200 uL. In some embodiments, the resuspension fluid is 5 uL, 10 uL, or 60 uL.

Another embodiment further comprises the step of conducting a molecular assay on the resuspended pellet to detect the presence of or quantify the amount of said ribonucleic acid component. In some embodiments, the molecular assay is selected from one or more of next generation sequencing (NGS), PCR, qPCR, RT-PCR, RT-qPCR, ddPCR, bioanalyzer, tapestation, qubit, nanodrop, ELISA, PCR-ELISA, MALDI-TOF, microarray, photometry, spectrophotometry, transmittance, turbidimetry, nephelometry, reflectometry, cytometry, amperometry, voltammetry, coulometry, nuclear run-on, ribosome profiling, Northern blotting, and in situ hybridization. In some embodiments, this molecular assay tests for the presence of a viral disease, such as COVID-19, SARS, or MERS.

In some embodiments, the contaminants is proteins, ribonucleases, deoxyribonucleases, proteases, albumin, lysing reagents, lysing salts, NaCl, KCl, $(NH_4)_2SO_4$, ammonium chloride, detergents, amphipathic molecules, non-ionic detergents, anionic detergents, cationic detergents, zwitterionic detergents, Triton X-100, Nonidet P-40, sodium deoxycholate, CHAPS, SDS, ethyl trimethyl ammonium bromide, metal ions, carbohydrates, glycerol, metal chelators, EDTA, reducing agents, Tris-2-carboxyethylphosphine hydrochloride (TCEP), carbon, cyanides, carbon monoxide, dithiothreitol (DTT), phosphites, hypophosphites, phosphorous acid, reducing sugars, ascorbic acid, formic acid, oxalic acid, diisobutylaluminum hydride, hydrazine, hydrogen peroxide, iodides, thiosulfates, dithionates, sulfur dioxide, sulfite compounds, compounds containing the $Sn2+$ ion, compounds containing the $Fe2+$ ion, sodium borohydride, diborane, zinc amalgam, sodium-lead alloy, sodium amalgam, nascent (atomic) hydrogen, lithium aluminum hydride, mercaptoethanol, ionic salts, non-ionic salts, or any combination thereof.

In some embodiments, the first phase solution and the second phase solution are selected from polymer-polymer, polymer-salt, alcohol-salt, micellar, reverse micellar, mixed micellar, ionic liquid, or short-chain alcohol. It shall be understood to one of skill in the art that polymer-polymer, for example, refers to an ATPS where the first phase solution is a polymer solution and the second phase solution is also a polymer solution. "Polymer-salt", on the other hand, refers to a first phase solution that is a polymer solution and a second phase solution that is a salt solution. In some embodiments, the first phase solution and the second phase solution is a polymer-salt combination. In some embodiments, the first phase solution is a 10-25% w/w polymer solution and the second phase solution is a 50%-70% w/w salt solution.

In some embodiments, the first phase solution comprises polymer components selected from polyethylene glycols (PEGs), hydrophobically modified polyethylene glycols, poly(oxyalkylene)polymers, poly(oxyalkylene)copolymers, hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide or any combination thereof.

In some embodiments, the molecular weight of said polymer is less than or equal to 2,000 Da. In some embodiments, the molecular weight of said polymer is less than or equal to 1,000 Da. In other embodiments, the molecular weight of said polymer is between 200 Da-1500 Da, 400 Da-1000 Da, 600 Da-1000 Da, or 700 Da-900 Da. In yet other embodiments, the molecular weight of said polymer is less than 1000 Da, 800 Da, 500 Da, or 200 Da. In yet other embodiments, the molecular weight of said polymer is less than 2000 Da, 1900 Da, 1800 Da, 1700 Da, 1600 Da, 1,500 Da, 1400 Da, 1300 Da, 1200 Da, 1100 Da, 1000 Da, 900 Da, 800 Da, 700 Da, 600 Da, 500 Da, 400 Da, 300 Da, 200 Da, or 100 Da.

Another aspect provides a composition for isolating ribonucleic acids from a fluid mixture including ribonucleic acids and contaminants, wherein said composition comprises a first phase component and a second phase component capable of forming an aqueous two phase system (ATPS); wherein the first phase component comprises a polymer having a molecular weight of less than 2,000 Da; and the second phase component comprises one or more salt components selected from the group consisting of ionic compounds and polyelectrolytes.

In some embodiments, the molecular weight of said polymer is less than or equal to 2,000 Da. In some embodiments, the molecular weight of said polymer is less than or equal to 1,000 Da. In other embodiments, the molecular weight of said polymer is between 200 Da-1500 Da, 400 Da-1000 Da, 600 Da-1000 Da, or 700 Da-900 Da. In yet other embodiments, the molecular weight of said polymer is less than 1000 Da, 800 Da, 500 Da, or 200 Da. In yet other embodiments, the molecular weight of said polymer is less than 2000 Da, 1900 Da, 1800 Da, 1700 Da, 1600 Da, 1,500 Da, 1400 Da, 1300 Da, 1200 Da, 1100 Da, 1000 Da, 900 Da, 800 Da, 700 Da, 600 Da, 500 Da, 400 Da, 300 Da, 200 Da, or 100 Da.

In some embodiments, the polymer is selected from the group consisting of polyethylene glycols (PEGs), hydrophobically modified polyethylene glycols, poly(oxyalkylene) polymers, poly(oxyalkylene)copolymers, hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide, EOPO, polypropylene glycol (PPG), polyacrylate, 3-(2-methylpropoxy)propan-1-ol (UCON™), or any combination thereof. In some embodiments, the polymer is polyethylene glycols (PEGs). EOPO is a copolymer mixture of ethylene oxide (EO) and propylene oxide (PO).

In some embodiments, the salt component is selected from the group consisting of inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium; inorganic salts containing anions such as phosphate, sulphate, nitrate, chloride and hydrogen carbonate; a kosmotropic salt, a chaotropic salt, a magnesium salt, a lithium salt, a sodium salt, a potassium salt, a cesium salt, a zinc salt, an aluminum salt, a bromide salt, an iodide salt, a fluoride salt, a carbonate salt, a sulfate salt, a citrate salt, a carboxylate salt, a borate salt, a phosphate salt, NaCl, $Na_2SO_4$, potassium citrate, sodium citrate, sodium acetate, sodium phosphate, potassium phosphate, ammonium sulfate, and ammonium acetate.

In some embodiments, the first phase component comprises a polymer selected from the group consisting of polyethylene glycol (PEG), polypropylene glycol (PPG), copolymer mixture of ethylene oxide and propylene oxide (EOPO), polyacrylate, and 3-(2-methylpropoxy)propan-1-ol (UCON™); and the second phase component comprises a salt selected from the group consisting of potassium phosphate, sodium citrate, sodium phosphate, ammonium sulfate, and sodium sulfate.

In some embodiments, the first phase component is PEG and the second phase component is potassium phosphate.

In some embodiments, the first phase component is PPG and the second phase component is sodium citrate.

In some embodiments, the first phase component is EOPO and the second phase component is sodium phosphate.

In some embodiments, the first phase component is polyacrylate and the second phase component is ammonium sulfate.

In some embodiments, the first phase component is 3-(2-methylpropoxy)propan-1-ol and the second phase component is sodium sulfate.

In some embodiments, the first phase and second phase solutions together form a total concentration of 10-25% w/w polymer and 50%-70% w/w salt. For the sake of clarity, the first phase and second phase solutions together make the ATPS, which has an overall concentration of 10-25% w/w polymer and 50%-70% w/w salt.

Another aspect provides a kit comprising any of the compositions described here.

In some embodiments, the kit further comprises one or more of the following reagents or powders: lysing reagent, buffer solution, precipitation salt, proteinase powder, reducing agent, co-precipitant solution, and carrier nucleic acid solution.

In some embodiments, the kit includes
23 mL of a buffer solution;
3 mL of a lysing reagent;
25×820 µL aliquots of a composition containing a first phase component and a second phase component as described herein;
2×7 mL aqueous solutions of a precipitation salt;
25 mg of a proteinase powder;
60 uL aqueous solution of co-precipitant; and optionally empty tubes.

In embodiments, the kit also includes
2×24 mg of a reducing agent; and
200 uL aqueous solution of a carrier nucleic acid.

In some embodiments, the aqueous solutions are made using DNase/RNase-free water.

Figure 1:
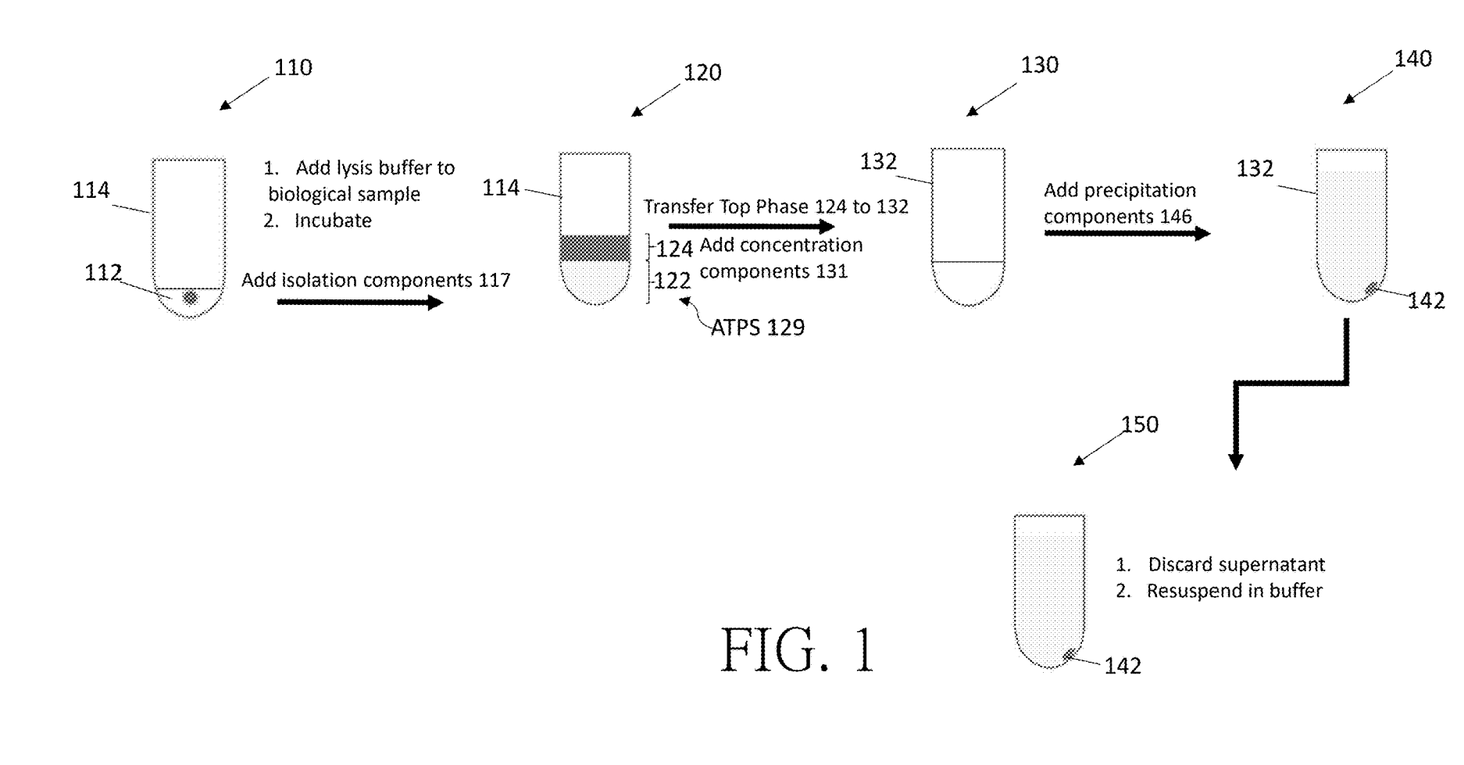
FIG. 1 is a schematic diagram which illustrates an example embodiment of a workflow for isolating and concentrating ribonucleic acids such as viral RNA from a fluid mixture.

Another aspect provides a method of isolating ribonucleic acids from a fluid mixture including ribonucleic acids and contaminants according to the steps shown in FIG. 1.

Another aspect provides a method of isolating ribonucleic acids from a fluid mixture including ribonucleic acids and contaminants using a kit described herein, comprising one or more of the following steps:

(a) adding 875 µL DNase/RNase-free water into one vial of proteinase powder (25 mg) and mixing well to form Solution B1; storing Solution B1 at 4° C.;

(b) adding 155 µL DNase/RNase-free water into one vial of reducing agent powder (24 mg) and mixing well to form Solution B2; storing Solution B2 at −20° C.;

(c) at room temperature, transferring 140-1000 µL of the fluid mixture into a 1.5 mL microcentrifuge tube; if necessary adding buffer solution such that the microcentrifuge tube contains 1 mL of liquid;

(d) adding the following reagents to the microcentrifuge tube in sequential order: 10 µL Solution B1; 11 µL Solution B2, 5.6 µL of a carrier nucleic acid solution; and 100 µL of a lysing reagent to form a mixture;

(e) vortexing the mixture and incubating it at room temperature for 10 minutes;

(f) briefly pipet-mixing the mixture and transferring the mixture into a tube of the composition to form Solution C;

(g) centrifuging Solution C tube and vortexing it until it is homogenous;

(h) centrifuging Solution C tube at 4,300×g for 1 minute to form a top phase and a clear bottom phase;

(i) extracting up to 120 µL of the top phase and transferring the top phase to a new 2 mL microcentrifuge tube without transferring any of the clear bottom phase;

(j) adding 230 µL DNase/RNase-free water to a new 2 mL microcentrifuge tube, if necessary, adding DNase/RNase-free water until the total volume is 350 µL;

(k) adding the following reagents to the new 2 mL microcentrifuge tube in sequential order: 510 µL a solution of precipitation salt, 2 µL of a solution of co-precipitant, and 860 µL of 100% isopropanol to form a second mixture;

(l) vortexing the second mixture until homogenous and incubating the second mixture at room temperature for 5 minutes;

(m) centrifuging the mixture at 4,300×g for 10 minutes;

(n) discarding all of the supernatant and adding 1 mL 40% isopropanol;

(o) centrifuging the mixture at 4,300×g for 2 minutes;

(p) discarding all of the supernatant and adding 1 mL 70% ethanol;

(q) centrifuging the mixture at 4,300×g for 2 minutes;

(r) discarding all of the supernatant;

(s) drying the pellet at room temperature for at least 10 min until completely dried;

(t) re-suspending the pellet in at least 10 µL of a resuspension buffer, and (u) adding a buffer directly to the dry pellet and pipette-mixing up and down 30 times or more.

In some embodiments, the proteinase is selected from the group consisting of Arg-C proteinase, BNPS-Skatole, Caspase3, Caspase6, Caspase9, Chymotrypsin-high specificity (C-term to [FYW], not before P), Clostripain (Clostridiopeptidase B), Factor Xa, GranzymeB, LysC, Neutrophil elastase, Pepsin (pH1.3), Proteinase K, Thermolysin, Asp-N endopeptidase, Caspase1, Caspase4, Caspase7, Caspase10, Chymotrypsin-low specificity (C-term to [FYWML], not before P), CNBr, Formic acid, Hydroxylamine, LysN, Pepsin, Staphylococcal peptidase I, Thrombin, Asp-N endopeptidase+N-terminal Glu, Caspase2, Caspase5, Caspase8, Enterokinase, Glutamyl endopeptidase, Iodosobenzoic acid, NTCB (2-nitro-5-thiocyanobenzoic acid), Proline-endopeptidase, Tobacco etch virus protease, and Trypsin. In some embodiments, the solution made from the proteinase powder has a concentration of 10-40 mg/mL.

In some embodiments, the reducing agent is selected from the group consisting of Tris-2-carboxyethylphosphine hydrochloride (TCEP), carbon, cyanides, carbon monoxide, dithiothreitol (DTI), phosphites, hypophosphites, phosphorous acid, reducing sugars, ascorbic acid, formic acid, oxalic acid, diisobutylaluminum hydride, hydrazine, hydrogen peroxide, iodides, thiosulfates, dithionates, sulfur dioxide, sulfite compounds, compounds containing the $Sn^{2+}$ ion, compounds containing the $Fe^{2+}$ ion, sodium borohydride, diborane, zinc amalgam, sodium-lead alloy, sodium amalgam, nascent (atomic) hydrogen, lithium aluminum hydride, mercaptoethanol. In some embodiments, the solution made from the reducing agent has a concentration of 50 to 250 mg/mL.

In some embodiments, the carrier nucleic acid is RNA or DNA. In some embodiments, the solution made from the carrier nucleic acid has a concentration of 0.2 to 2 ug/uL.

In some embodiments, the lysing reagent is selected from the group consisting of lysing salts, NaCl, KCl, $(NH_4)_2SO_4$, guanidinium hydrochloride, ammonium chloride, detergents, amphipathic molecules, non-ionic detergents, anionic detergents, cationic detergents, zwitterionic detergents, Triton X-100, Nonidet P-40, sodium deoxycholate, CHAPS, SDS, ethyl trimethyl ammonium bromide, metal ions, carbohydrates, glycerol, metal chelators, and EDTA. In some embodiments, the lysing reagent has a concentration of 2M-20M.

In some embodiments, the precipitation salt is selected from the group consisting of sodium acetate, ammonium acetate, sodium chloride, lithium chloride, sodium iodide, and potassium acetate. In some embodiments, the precipitation salt has a concentration of 5M-10M.

In some embodiments, the co-precipitant is selected from the group consisting of PEG, linear polyacrylamide, glycogen, RNA, DNA. In some embodiments, the solution containing the co-precipitant is 80 to 100% w/w.

Preparation of Sample

A biological sample may be collected via one or more of the following methods: throat swab, nasal swab, saliva swab, saliva sample, stimulate saliva sample, expectorated sputum, bile sample, urine sample, vaginal swab, endocervical swab, urethral swab, semen sample, blood sample, plasma sample, serum sample, fecal sample, cerebral spinal fluid, lacrimal fluid sample, perspiration fluid sample, amniotic fluid sample, or tissue biopsy. The biological sample may be selected from the group consisting of saliva, expectorated sputum, urine, bile, vaginal fluid, endocervical fluid, urethral fluid, semen, blood, plasma, serum, feces, cerebral spinal fluid, lacrimal fluid, perspiration, amniotic fluid, and a tissue biopsy. The biological sample to be tested is resuspended in a suitable viral transfer medium in a suitable volume to become a sample mixture. It should be understood that when a biological sample is a "swab", it is referring to biological sample from a subject that is obtained as a result of conducting the act of swabbing a particular part of the subject's body. A throat swab, for example, involves using a swab to obtaining sample from a subject's throat. This sample could contain, for example, saliva, throat cells, bacterial or viruses, and the like, all of which combine to become the biological sample referred to as a "throat swab", which can optionally be suspended into a liquid medium and put into a container for storage, transfer, or testing.

With reference to FIG. 1, an example method embodiment may include an optional first step 110 of preparing a fluid mixture by mixing in a suitable vessel 114 with a biological sample 112 (i.e., a sample mixture in viral transfer medium) and a lysis buffer and incubating for a sufficient time (e.g., preferably within a range of 1 to 60 minutes) at a proper temperature (e.g., in a range from 15° to 40° C.) to release nucleic acids from cells, exosomes, proteins and/or other materials in the biological sample. In certain example embodiments, the lysis buffer may have a pH in the range of from 4 to 11, of from 7 to 10 or of from 8 to 9. The concentration of substances in the lysis buffer depends on the amount of biologic material to be lysed and the manner of the provision of said biologic material. In principle, any separating methods known to the skilled worker may be suitable for releasing nucleic acids from the biological sample. Lysis methods which may be contemplated are in particular lysis by the action of heat, lysis by the action of mechanical force, lysis by enzymes such as, for example, protein kinase K, or lysis by contacting the cells to a lysis buffer containing a detergent or a chaotropic compound, or by means of hypotonic solutions. Where appropriate, the abovementioned measures may also be combined, for example by mechanically disrupting the cells in a lysis buffer containing a detergent or a chaotropic compound or, for example, by employing a lysis buffer containing protein kinase K together with a chaotropic compound. In certain embodiments, the sample mixture and the lysis buffer may be vortexed and incubated at room temperature.

Isolation of Analyte

Isolation components 117 may be added into the fluid mixture, in an isolation step 120, forming an aqueous two-phase system with new ATPS component concentrations, ATPS 129, with or without centrifugation, in order to separate target ribonucleic acid from contaminants. The isolation components 117 may include a first phase forming polymer component dissolved in a first phase solution 124, and a second phase solution 122, such that the target ribonucleic acids partition into the first phase solution 124 (e.g., a polymer-rich upper phase) while proteins and other contaminants partition to the second phase solution 122 (e.g., a salt-rich lower phase).

A number of types of ATPS 129 may be utilized, including polymer-salt systems, polymer-polymer systems, and polymer-surfactant systems. Phase separation partitioning may be affected by factors such as appropriate selection and specific ordering of the isolation components 117, pH, molecular weight, relative concentrations, as well as centrifugation, mixing and incubation steps.

The isolation components 117 may include polymer components that assist in forming first phase solution 124 and second phase solution 122. Suitable polymers may include polyethylene glycols (PEGs), hydrophobically modified polyethylene glycols, poly(oxyalkylene)polymers, poly(oxyalkylene)copolymers, hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide, copolymer mixture of ethylene oxide and propylene oxide (EOPO), polypropylene glycol (PPG), polyacrylate, and 3-(2-methylpropoxy)propan-1-ol (UCON™), or any combination thereof.

In a polymer-salt embodiment of ATPS 129, second phase solution 122 may include a dissolved salt. Suitable salts include, but are not limited to inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium; inorganic salts containing anions such as phosphate, sulphate, nitrate, chloride and hydrogen carbonate; a kosmotropic salt, a chaotropic salt, a magnesium salt, a lithium salt, a sodium salt, a potassium salt, a cesium salt, a zinc salt, an aluminum salt, a bromide salt, an iodide salt, a fluoride salt, a carbonate salt, a sulfate salt, a citrate salt, a carboxylate salt, a borate salt, a phosphate salt, NaCl, $Na_2SO_4$, potassium citrate, sodium citrate, sodium acetate, sodium phosphate, potassium phosphate, ammonium sulfate, and ammonium acetate.

In some embodiments, the first phase solution 124 is formed containing a polymer having a mean molecular weight of less than or equal to 2,000 Da (e.g., 100, 200, 300, 400, 500, 600, 700, 800, 900, 1000, 1100, 1200, 1300, 1400, 1500, 1600, 1700, 1800, 1900, 2000 Da.)

Transfer of Analyte

In step 130, the top phase 124 is transferred to vessel 132. In some embodiments, an amount of the top phase may be left behind.

Concentration of Analyte

It is desirable to decrease the process volume of the working solution containing the target ribonucleic acid. In an ATPS, this can be achieved by decreasing the volume of the top-phase.

Recovery of Analyte

In optional recovery step 140, the concentrated target ribonucleic acid may be combined with precipitation components, with centrifugation, in order to isolate and desalinate the target ribonucleic acid from the solution as pellet 142 formed at the bottom of vessel 132. In step 150, supernatant may be removed and pellet 142 comprised of target ribonucleic acid may be resuspended in a suitable buffer.

EXAMPLES

The present invention will be described in more detail with reference to the following examples. One skilled in the art will readily appreciate that the examples provided are merely for illustrative purposes and are not meant to limit the scope of the invention which is defined by the claims following thereafter. All references given below and elsewhere in the present application are hereby included by reference.

Example 1—Partitioning of Nucleic Adds to Different Phases in ATPS

Experiments were performed by spiking known nucleic acids quantities into the different ATPS compositions, mixing thoroughly, and allowing sufficient time for phase separation. After phase separation, both phases were extracted and the nucleic acid content was determined using a variety of assays (gel electrophoresis, spectrophotometry, qPCR, ddPCR, and bioanalysis).

Results:

Nucleic acids partition to different phases depending on the molecular weight of the polymer as well as the concentrations of polymer and salt in the aqueous two-phase system. When the polymer molecular weight was less than or equal to 400 g/mol, almost all nucleic acids tend to partition to the top phase, regardless of the concentrations. When polymer molecular weight was greater than or equal to 4600 g/mol, nucleic acids tend to partition to the bottom phase. When the polymer molecular weight was between 600 g/mol and 1500 g/mol, nucleic acid partitioning depends on the concentrations of ATPS components, however we were able to find concentrations that result in the nucleic acids partitioning preferentially to the top phase.

Summary of Data shown in Table 1 as below. The percentages describe the relative quantity of nucleic acids partition to the respective phase. Experiments were done in a variety of different polymer and salt concentrations. The below results are an average of all the experiments done.

TABLE 1

Summarized Data on the percentages describe the relative quantity of nucleic acids partition to the respective phase.

| Polymer MW (g/mol) | Partition to Top Phase | Partition to Bottom Phase |
| --- | --- | --- |
| 200 | >95% | <5% |
| 300 | >95% | <5% |
| 400 | >95% | <5% |
| 600 | >75% | <25% |
| 1000 | >75% | <25% |
| 1500 | >75% | <25% |
| 4600 | <25% | >75% |
| 8000 | <5% | >95% |

Example 2—Method of Isolating Viral RNA from a Biological Sample

Preparation of Materials and Reagents

The following reagents are required for the method:

Top up buffer stored at room temperature, for example, 15-30° C.

Lysing agent [2 to 20M]

ATPS

Proteinase [10-40 mg/mL] resuspended in water and stored at cold temperatures, such as 4° C.

Precipitation salt [5 to 10M]

Co-precipitant [80 to 100% w/w]

Reducing agent [50 to 250 mg/mL] resuspended in water and stored at chilled temperatures, such as −20° C. (optional)

Carrier nucleic acid [0.2 to 2 ug/ul](optional)

Method of Isolating Viral RNA from a Biological Sample

Figure 2:
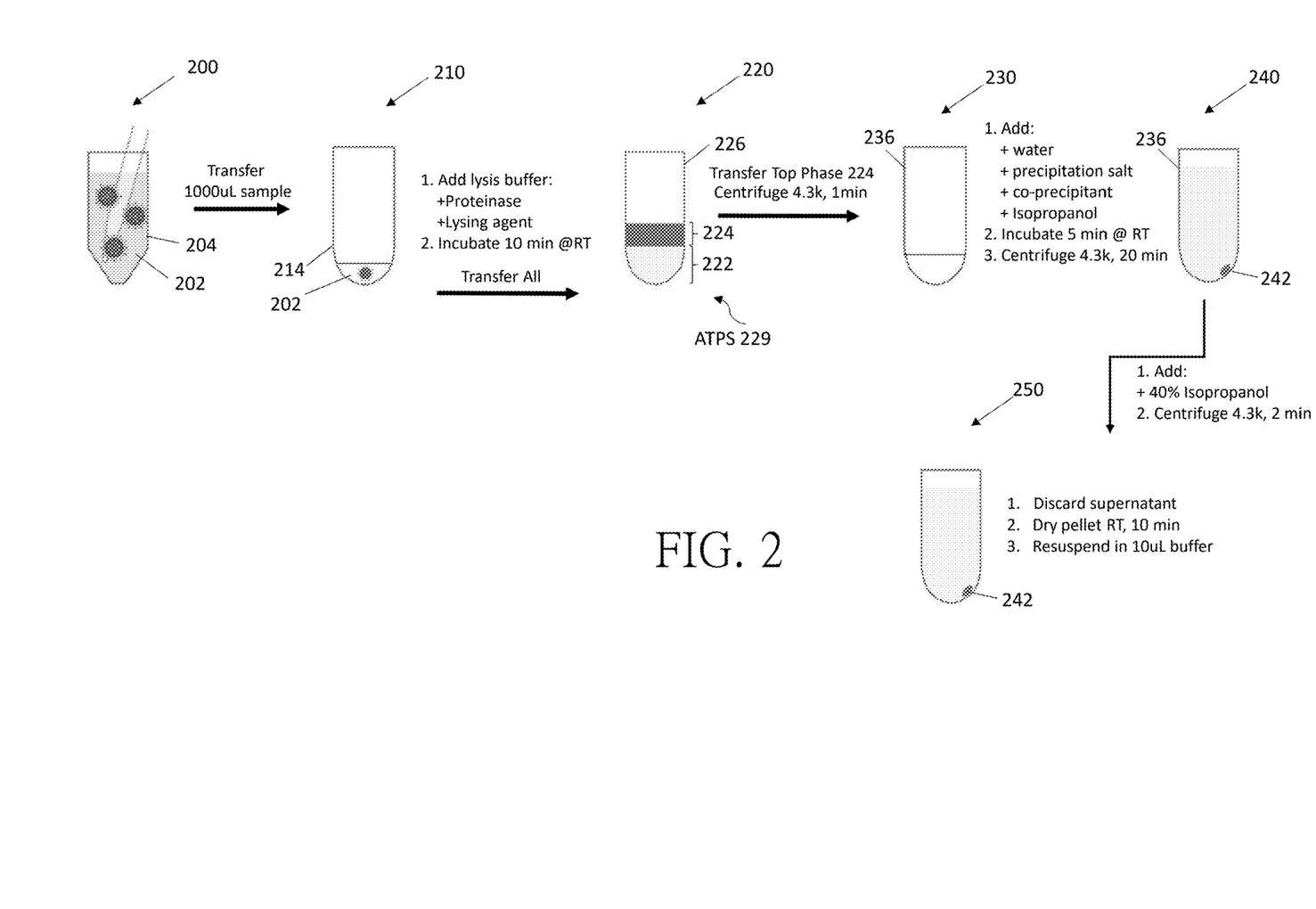
FIG. 2 is a schematic diagram which illustrates another example embodiment of a workflow for isolating and concentrating ribonucleic acids such as viral RNA from a fluid mixture.

With reference to FIG. 2, a sample such as a nasal or deep throat swab of a subject is immersed in a suitable volume (for example, 1, 2, 3, 4, 5, 6, 7, 8, 9, 10 ml or more) of viral transfer medium to form a sample mixture 202 in an optional step 200. The sample may or may not contain the viral RNA of interest Transfer a suitable amount of the sample mixture 202 into a suitable vessel. In this embodiment, the amount of the sample mixture 202 used is 1000 ul. In this embodiment, the suitable vessel is a microcentrifuge tube 204. If less than 1000 ul of sample mixture 202 is available, the final volume may be made up with medium suitable top up buffer to obtain a final volume of 1000 ul of sample mixture. The 1000 ul sample mixture may be optionally transferred to a new vessel.

In the optional step 210, a suitable volume (such as 10 ul) of Proteinase solution, and a suitable volume (such as 100 ul) lysing agent (together as the lysis buffer) are added into the sample mixture to form a fluid mixture. Optionally, a suitable volume (such as 11 ul) of reducing agent and a suitable amount (such as 5.6 ul) carrier nucleic acid are added into the sample mixture. The fluid mixture is vortexed to mix. The fluid mixture is incubated at room temperature (such as 15-30° C.) for 10 minutes. In certain example embodiments, the proteinase solution may contain one or more of Arg-C proteinase, BNPS-Skatole, Caspase3, Caspase6, Caspase9, Chymotrypsin-high specificity (C-term to [FYW], not before P), Clostripain (Clostridiopeptidase B), Factor Xa, GranzymeB, LysC, Neutrophil elastase, Pepsin (pH1.3), Proteinase K, Thermolysin, Asp-N endopeptidase, Caspase1, Caspase4, Caspase7, Caspase10, Chymotrypsin-low specificity (C-term to [FYWML], not before P), CNBr, Formic acid, Hydroxylamine, LysN, Pepsin, Staphylococcal peptidase I, Thrombin, Asp-N endopeptidase+N-terminal Glu, Caspase2, Caspase5, Caspase8, Enterokinase, Glutamyl endopeptidase, Iodosobenzoic acid, NTCB (2-nitro-5-thiocyanobenzoic acid), Proline-endopeptidase, Tobacco etch virus protease and Trypsin. In certain embodiments, the lysing agent may contain one or more of lysing salts, NaCl, KCl, $(NH_4)_2SO_4$, guanidinium hydrochloride, ammonium chloride, detergents, amphipathic molecules, non-ionic detergents, anionic detergents, cationic detergents, zwitterionic detergents, Triton X-100, Nonidet P-40, sodium deoxycholate, CHAPS, SDS, ethyl trimethyl ammonium bromide, metal ions, carbohydrates, glycerol, metal chelators and EDTA. In certain example embodiments, the reducing agent may contain one or more of Tris-2-carboxyethylphosphine hydrochloride (TCEP), carbon, cyanides, carbon monoxide, dithiothreitol (DTT), phosphites, hypophosphites, phosphorous acid, reducing sugars, ascorbic acid, formic acid, oxalic acid, diisobutylaluminum hydride, hydrazine, hydrogen peroxide, iodides, thiosulfates, dithionates, sulfur dioxide, sulfite compounds, compounds containing the Sn2+ ion, compounds containing the Fe2+ ion, sodium borohydride, diborane, zinc amalgam, sodium-lead alloy, sodium amalgam, nascent (atomic) hydrogen, lithium aluminum hydride, mercaptoethanol. In certain embodiments, the carrier nucleic acid may contain RNA and/or DNA.

The fluid mixture is optionally further mixed with any suitable fluid transfer means such as an autopipette or a pipette. In step 220, the entire contents are transferred to a new vessel such as a tube 226 containing isolation components to form an aqueous two-phase (ATPS) system 229 (or the isolation mixture). In one example embodiment, the tube 226 containing isolation components is briefly centrifuged before use. The isolation mixture is vortexed until the mixture becomes homogenous. The isolation mixture then is briefly centrifuged to separate two phases, the top phase 224 and the bottom phase 222. In this example embodiment, the isolation mixture is centrifuged at around 4,300×g for 1 minute. In certain example embodiments, the ATPS system 229 forms from a first phase component and a second phase component. The first phase component comprises a polymer having a molecular weight of less than 2,000 Da and the second phase component comprises one or more salt components selected from the group consisting of ionic compounds and polyelectrolytes. In one example embodiment, the first phase component contains a polymer having a molecular weight of less than 2,000 Da. In one example embodiment, the first phase component contains a polymer selected from the group consisting of PEG, PPG, EOPO, polyacrylate, and UCON (CAS #69226-89-73, such as (2-Methylpropoxy) propan-1-ol) and the second phase component contains a salt selected from the group consisting of potassium phosphate, sodium citrate, sodium phosphate, ammonium sulfate, and sodium sulfate.

A suitable volume (such as 120 ul) of the top phase 224 is extracted and transferred to a new vessel 236 with any suitable fluid transfer means such as an autopipette or pipette. In certain example embodiments, if less than 120 ul of the top phase 224 is available, the top phase 224 is extracted as much as possible. In one example embodiment, the vessel 226 may be tilted at a certain angle to collect the top phase 224 along the vessel wall to avoid transferring any of the bottom phase 222.

In step 230, a suitable volume (such as 260 ul) of water is added to the top phase 224. In certain embodiments, if less than 120 ul top phase 224 was transferred, add enough water to top up to a final volume of 350 ul. In this embodiment, the water is deionized water. In some embodiments, the water is RNase free and/or DNase free. A suitable volume (such as 580 ul) solution precipitation salt, a suitable volume (such as 2 ul) co-precipitant, a suitable volume (such as 980 ul) 100% isopropanol were added to the mixture. The mixture is optionally vortexed to form a homogenous solution. The mixture is incubated at room temperature for a suitable time, such as 5 minutes. The mixture is then centrifuged at around 4,300×g for 5-20 minutes or longer. In this embodiment, the mixture is then centrifuged at around 4,300×g for 20 minutes. In certain example embodiments, the precipitation salt may contain one or more of sodium acetate, ammonium acetate, sodium chloride, lithium chloride, sodium iodide and potassium acetate. In certain example embodiments, the co-precipitant may contain one or more of PEG, linear polyacrylamide, glycogen, RNA and DNA.

In step 240, all supernatant is discarded, leaving the pellet 242. A suitable volume (such as 1 ml) 40% isopropanol is added to the vessel 236. The vessel 236 is centrifuged at around 4,300×g for 2 minutes.

In step 250, all supernatant is discarded. The pellet 242 is dried at room temperature until the pellet 242 is completely dried. In one example embodiment, the pellet 242 is dried for at least 10 minutes. The pellet is resuspended in a desired volume of a suitable resuspension buffer, such as 5 ul, 6 ul, 7 ul, 8 ul, 9 ul, 10 ul, 11 ul, 12 ul, 13 ul, 14 ul, 15 ul, 16 ul, 17 ul, 18 ul, 19 ul, 20 ul, 40 ul, 100 ul or more. In this embodiment, the desired volume is 10 ul. In one example embodiment, the resuspension buffer is added directly to the pellet and mixed up and down with an autopipette. In one example embodiment, the resuspension buffer may be water. In another example embodiment, the resuspension buffer may be a buffer compatible with the downstream analysis.

Example 3—Selection of Reagents for Lysis Buffer: Lysing Agent, Reducing Agent and/or Carrier Nucleic Acid Experiments were performed by spiking known copies of ribonucleic acids in the same quantities using different lysis buffer combinations (i.e., proteinase with or without lysing agent, reducing agent and/or carrier nucleic acid) with the same isolation method as described in Example 2. The same proteinase, ATS, precipitation salt and co-precipitant in the same amounts were used. After phase separation, both phases were extracted and the ribonucleic acid content was determined using qPCR analysis. For each reaction, 10 ul working solution plus 10 ul elute were used.

Results:

Table 2 below shows the summarized data. The data shows that the reducing agent is not necessary, indicating that the lysing agent can function as both the reducing reagent/RNase inhibitor and lysing reagent. The data also shows that the carrier nucleic acid is not necessary.

TABLE 2

Summarized Data on the selection of the reagents.

| Reaction | Biological replicate | Spike-in copies | ID | Ct | | | | |
|---|---|---|---|---|---|---|---|---|
| | | | | 1st replicate | 2nd replicate | 3rd replicate | Average Ct | SD |
| Control | 3 | 7500 | 1 | 32.06 | 32.07 | 32 | 32.04 | 0.04 |
| No reducing reagent | 3 | 7500 | 2 | 31.16 | 31.33 | 31.12 | 31.20 | 0.11 |
| No carrier RNA | 3 | 7500 | 3 | 30.57 | 30.67 | 30.47 | 30.57 | 0.10 |
| No reducing reagent or carrier RNA | 3 | 7500 | 4 | 30.22 | 30.28 | 30.36 | 30.29 | 0.07 |
| NTC | 1 | N/A | | ND | ND | ND | / | / |

Control-Reaction using proteinase, lysing agent, reducing agent and carrier nucleic acid;
No reducing reagent-Reaction using proteinase, lysing agent and carrier nucleic acid without reducing agent;
No carrier RNA-Reaction using proteinase, lysing agent, and reducing agent without carrier nucleic acid;
No reducing reagent or carrier RNA-Reaction using proteinase, lysing agent without reducing agent nor carrier nucleic acid;
NTC = Negative control; ND = not detected; N/A = Not available.

The exemplary embodiments of the present invention are thus fully described. Although the description referred to particular embodiments, it will be clear to one skilled in the art that the present invention may be practiced with a variation of these specific details. Hence this invention should not be construed as limited to the embodiments set forth herein.

The invention claimed is:

1. A method for isolating ribonucleic acids (RNAs) from a fluid mixture containing RNAs and proteins, wherein the method comprises:
   (a) providing a biological sample;
   (b) mixing the biological sample with a lysing reagent to form a sample mixture, wherein the lysing reagent has a concentration of 2M-20M, and the lysing reagent is a lysing salt or a detergent, wherein
      the lysing salt is selected from the group consisting of NaCl, KCl, (NH$_4$)$_2$SO$_4$, guanidinium hydrochloride and ammonium chloride; and
      the detergent is selected from the group consisting of Triton X-100, Nonidet P-40, sodium deoxycholate, sodium dodecyl sulfate (SDS), 3-((3-cholamidopropyl) dimethylammonio)-1-propanesulfonate (CHAPS), and ethyl trimethyl ammonium bromide;
   (c) incubating the sample mixture to arrive at the fluid mixture;
   (d) adding said fluid mixture to an aqueous two-phase system (ATPS) comprising a first phase solution and a second phase solution, wherein the first phase solution comprises 10-25% w/w polymer and the second phase solution comprises 50-70% w/w salt, wherein the polymer has a molecular weight of less than 2,000 Da and is selected from the group consisting of polyethylene glycol (PEG), polypropylene glycol (PPG), copolymer mixture of ethylene oxide and propylene oxide (EOPO), polyacrylate, and 3-(2-methylpropoxy)propan-1-ol; and the salt is selected from the group consisting of potassium phosphate, sodium citrate, sodium phosphate, ammonium sulfate, and sodium sulfate; such that the RNAs partition to the first phase solution and said proteins partition to the second phase solution; and
   (e) isolating the RNAs from the first phase solution.

2. The method of claim 1, wherein the ribonucleic acids (RNAs) are ribonucleic acid (RNA) fragments under 250 bp.

3. The method of claim 1, wherein said biological sample comprises biological material that releases RNAs when mixing with the lysis reagent.

4. The method of claim 3, where the biological material is selected from the group consisting of: viruses, eukaryotic cells, prokaryotic cells, protein coats, vesicles, and RNA complexed with proteins.

5. The method of claim 4, wherein the biological material is a virus.

6. The method of claim 5, wherein the virus is an enveloped virus with a lipid bilayer.

7. The method of claim 5, wherein the virus has a target viral RNA that is in complex in a nucleocapsid within the viral envelope of said virus.

8. The method of claim 5, wherein the virus is selected from the group consisting of: Yueviridae, Xinmoviridae, Wupedeviridae, Virgaviridae, Tymoviridae, Turriviridae, Tristromaviridae, Totiviridae, Tospoviridae, Tombusviridae, Tolecusatellitidae, Togaviridae, Tobaniviridae, Tectiviridae, Sunviridae, Spiraviridae, Sphaerolipoviridae, Solinviviridae, Solemoviridae, Smacoviridae, Siphoviridae, Secoviridae, Sarthroviridae, Rudiviridae, Roniviridae, Rhabdoviridae, Retroviridae, Reoviridae, Quadriviridae, Qinviridae, Pseudoviridae, Poxviridae, Potyviridae, Pospiviroidae, Portogloboviridae, Polyomaviridae, Polydnaviridae, Polycipiviridae, Podoviridae, Pneumoviridae, Pleolipoviridae, Plasmaviridae, Picomaviridae, Picobimaviridae, Phycodnaviridae, Phenuiviridae, Phasmaviridae, Permutotetraviridae, Peribunyaviridae, Parvoviridae, Partitiviridae, Paramyxoviridae, Papillomaviridae, Ovaliviridae, Orthomyxoviridae, Nyamiviridae, Nudiviridae, Nodaviridae, Nimaviridae, Namaviridae, Nanoviridae, Nairoviridae, Mypoviridae, Myoviridae, Mymonaviridae, Mononiviridae, Mimiviridae, Microviridae, Metaviridae, Mesoniviridae, Megabirnaviridae, Medioniviridae, Matonaviridae, Marseilleviridae, Marnaviridae, Malacoherpesviridae, Luteoviridae, Lispiviridae, Lipothrixviridae, Leviviridae, Leishbuviridae, Lavidaviridae, Kitaviridae, Iridoviridae, Inoviridae, Iflaviridae, Hytrosaviridae, Hypoviridae, Herpesviridae, Herelleviridae, Hepeviridae, Hepadnaviridae, Hantaviridae, Guttaviridae, Globuloviridae, Genomoviridae, Geminiviridae, Gammaflexiviridae, Fuselloviridae, Flaviviridae, Fimoviridae, Filoviridae, Euroniviridae, Endornaviridae, Dicistroviridae, Deltaflexiviridae, Cystoviridae, Cruliviridae, Corticoviridae, Coronaviridae, Closteroviridae, Clavaviridae, Circoviridae, Chuviridae, Chrysoviridae, Caulimoviridae, Carmotetraviridae, Caliciviridae, Bromoviridae, Botourmiaviridae, Bornaviridae, Bimaviridae, Bidnaviridae, Bicaudaviridae, Betaflexiviridae, Benyviridae, Belpaoviridae, Barnaviridae, Baculoviridae, Bacilladnaviridae, Avsunviroidae, Astroviridae, Aspiviridae, Asfarviridae, Ascoviridae, Artoviridae, Arteriviridae, Arenaviridae, Anelloviridae, Ampullaviridae, Amnoonviridae, Amalgaviridae, Alvernaviridae, Alphatetraviridae, Alphasatellitidae, Alphaflexiviridae, Alloherpesviridae, Adenoviridae, Ackermannviridae, and Abyssoviridae.

9. The method of claim 8, wherein the Coronaviridae is SAR-CoV, SARS-CoV-2, or MERS-CoV.

10. The method of claim 1, wherein the fluid mixture is 1 uL to 1000 uL.

11. The method of claim 1, further comprising the step of collecting the biological sample from a subject.

12. The method of claim 11, wherein the biological sample is selected from the group consisting of: throat swab, nasal swab, saliva swab, saliva sample, stimulate saliva sample, expectorated sputum, bile sample, urine sample, vaginal swab, endocervical swab, urethral swab, semen sample, blood sample, plasma sample, serum sample, fecal sample, cerebral spinal fluid, lacrimal fluid sample, perspiration fluid sample, amniotic fluid sample, and tissue biopsy.

13. The method of claim 11, wherein the biological sample is selected from the group consisting of saliva, expectorated sputum, urine, bile, vaginal fluid, endocervical fluid, urethral fluid, semen, blood, plasma, serum, feces, cerebral spinal fluid, lacrimal fluid, perspiration, amniotic fluid, and a tissue biopsy.

14. The method of claim 1, wherein isolating the RNAs from the first phase solution comprises the following steps:
   i) mixing the first phase solution with RNA precipitation components to form a mixed solution;
   ii) centrifuging the mixed solution to form a pellet containing the ribonucleic acid; and
   iii) re-suspending the pellet containing the ribonucleic acid in a resuspension fluid to form a re-suspended pellet.

15. The method of claim 14, wherein the volume of the resuspension fluid is 5 uL-200 uL.

16. The method of claim 14, further comprising the step of conducting a molecular assay on the resuspended pellet to detect the presence of or quantify the amount of said RNAs.

17. The method of claim 16, wherein the molecular assay is selected from the group consisting of next generation sequencing (NGS), polymerase chain reaction (PCR), quantitative polymerase chain reaction (qPCR), reverse transcription polymerase chain reaction (RT-PCR), quantitative reverse transcription polymerase chain reaction (RT-qPCR), droplet digital polymerase chain reaction (ddPCR), bioanalyzer, tapestation, qubit, nanodrop, enzyme-linked immunosorbent assay (ELISA), polymerase chain reaction-enzyme linked immunosorbent assay (PCR-ELISA), matrix-assisted laser desorption/ionization-time of flight (MALDI-TOF), microarray, photometry, spectrophotometry, transmittance, turbidimetry, nephelometry, reflectometry, cytometry, amperometry, voltammetry, coulometry, nuclear run-on, ribosome profiling, Northern blotting, and in situ hybridization.

18. The method of claim 1, wherein the molecular weight of said polymer is between 200 Da-1500 Da, 400 Da-1000 Da, 600 Da-1000 Da, or 700 Da-900 Da.

19. The method of claim 1, wherein the molecular weight of said polymer is less than 1000 Da, 800 Da, 500 Da, or 200 Da.

20. The method of claim 1, wherein the molecular weight of said polymer is less than 2000 Da, 1900 Da, 1800 Da, 1700 Da, 1600 Da, 1,500 Da, 1400 Da, 1300 Da, 1200 Da, 1100 Da, 1000 Da, 900 Da, 800 Da, 700 Da, 600 Da, 500 Da, 400 Da, 300 Da, 200 Da, or 100 Da.

21. A method of isolating ribonucleic acids (RNAs) from a fluid mixture containing RNAs and proteins, the method comprises the following steps:
  (a) adding 875 µL DNase/RNase-free water into one vial of proteinase powder (25 mg) and mixing well to form Solution B1; storing Solution B1 at 4° C.;
  (b) adding 155 µL DNase/RNase-free water into one vial of reducing agent powder (24 mg) and mixing well to form Solution B2; storing Solution B2 at −20° C.;
  (c) at room temperature, transferring 140-1000 µL of the fluid mixture into a 1.5 mL microcentrifuge tube; if necessary adding buffer solution such that the 1.5 mL microcentrifuge tube contains 1 mL of liquid;
  (d) adding the following reagents to the microcentrifuge tube in sequential order: 10 µL Solution B1; 11 µL Solution B2, 5.6 µL of a carrier nucleic acid solution; and 100 µL of a lysing reagent to form a mixture, wherein the lysing reagent has a concentration of 2M-20M, and the lysing reagent is a lysing salt or a detergent, wherein
    the lysing salt is selected from the group consisting of NaCl, KCl, $(NH_4)_2SO_4$, guanidinium hydrochloride and ammonium chloride; and
    the detergent is selected from the group consisting of Triton X-100, Nonidet P-40, sodium deoxycholate, sodium dodecyl sulfate (SDS), 3-((3-cholamidopropyl) dimethylammonio)-1-propanesulfonate (CHAPS), and ethyl trimethyl ammonium bromide;
  (e) vortexing the mixture and incubating it at room temperature for 10 minutes;
  (f) briefly pipet-mixing the mixture and transferring the mixture into a tube of a composition to form Solution C, wherein the composition comprises a first phase component and a second phase component capable of forming an aqueous two phase system (ATPS); wherein the first phase component comprises 10-25% w/w polymer and the second phase component comprises 50-70% w/w salt, wherein the polymer has a molecular weight of less than 2,000 Da and is selected from the group consisting of polyethylene glycol (PEG), polypropylene glycol (PPG), copolymer mixture of ethylene oxide and propylene oxide (EOPO), polyacrylate, and 3-(2-methylpropoxy)propan-1-ol; wherein the salt is selected from the group consisting of potassium phosphate, sodium citrate, sodium phosphate, ammonium sulfate, and sodium sulfate;
  (g) centrifuging Solution C tube and vortexing it until it is homogenous;
  (h) centrifuging Solution C tube at 4,300×g for 1 minute to form a first phase solution comprising the first phase component and a second phase solution comprising the second phase component, such that the RNAs partition to the first phase solution and said proteins partition to the second phase solution;
  (i) extracting up to 120 µL of the top phase and transferring the top phase to a new 2 mL microcentrifuge tube without transferring any of the clear bottom phase;
  (j) adding 230 µL DNase/Rnase-free water to a new 2 mL microcentrifuge tube, if necessary, adding DNase/Rnase-free water until the total volume is 350 µL;
  (k) adding the following reagents to the new 2 mL microcentrifuge tube in sequential order: 510 µL a solution of precipitation salt, 2 µL of a solution of co-precipitant, and 860 µL of 100% isopropanol to form a second mixture;
  (l) vortexing the second mixture until homogenous and incubating the second mixture at room temperature for 5 minutes;
  (m) centrifuging the mixture at 4,300×g for 10 minutes;
  (n) discarding all of the supernatant and adding 1 mL 40% isopropanol;
  (o) centrifuging the mixture at 4,300×g for 2 minutes;
  (p) discarding all of the supernatant and adding 1 mL 70% ethanol;
  (q) centrifuging the mixture at 4,300×g for 2 minutes;
  (r) discarding all of the supernatant, leaving a pellet containing the RNAs;
  (s) drying the pellet at room temperature for at least 10 min until completely dried;
  (t) re-suspending the pellet in at least 10 µL of a resuspension buffer; and
  (u) adding a buffer directly to the dry pellet and pipette-mixing up and down 30 times or more, thereby obtaining the isolated RNAs.

22. The method of claim 21, wherein
  the proteinase is selected from the group consisting of Arg-C proteinase, BNPS-Skatole, Caspase3, Caspase6, Caspase9, Chymotrypsin-high specificity (C-term to [FYW], not before P), Clostripain (Clostridiopeptidase B), Factor Xa, GranzymeB, LysC, Neutrophil elastase, Pepsin (pH1.3), Proteinase K, Thermolysin, Asp-N endopeptidase, Caspase1, Caspase4, Caspase7, Caspase10, Chymotrypsin-low specificity (C-term to [FYWML], not before P), CNBr, Formic acid, Hydroxylamine, LysN, Pepsin, Staphylococcal peptidase I, Thrombin, Asp-N endopeptidase+N-terminal Glu, Caspase2, Caspase5, Caspase8, Enterokinase, Glutamyl endopeptidase, Iodosobenzoic acid, NTCB (2-nitro-5-thiocyanobenzoic acid), Proline-endopeptidase, Tobacco etch virus protease, and Trypsin;
  the reducing agent is selected from the group consisting of Tris-2-carboxyethylphosphine hydrochloride (TCEP), carbon, cyanides, carbon monoxide, dithiothreitol (DTT), phosphites, hypophosphites, phosphorous acid, reducing sugars, ascorbic acid, formic acid, oxalic acid, diisobutylaluminium hydride, hydrazine, iodides, thiosulfates, dithionates, sulfur dioxide, sulfite compounds, compounds containing the Sn2+ ion, compounds containing the Fe2+ ion, sodium borohydride, diborane, zinc amalgam, sodium-lead alloy, sodium amalgam, nascent (atomic) hydrogen, lithium aluminium hydride, mercaptoethanol;

the carrier nucleic acid is RNA or DNA;

the precipitation salt is selected from the group consisting of sodium acetate, ammonium acetate, sodium chloride, lithium chloride, sodium iodide, and potassium acetate; and the co-precipitant is selected from the group consisting of PEG, linear polyacrylamide, glycogen, RNA, DNA.

23. The method of claim 21, wherein the solution made from the proteinase powder has a concentration of 10-40 mg/mL;

the solution made from the reducing agent has a concentration of 50 to 250 mg/mL;

the solution made from the carrier nucleic acid has a concentration of 0.2 to 2 ug/uL;

the precipitation salt has a concentration of 5M-10M; and the solution containing the co-precipitant is 80 to 100% w/w.

24. The method of claim 21, wherein the ribonucleic acids (RNAs) are ribonucleic acid (RNA) fragments under 250 bp.

* * * * *